United States Patent
Zhang et al.

(10) Patent No.: US 8,636,627 B2
(45) Date of Patent: Jan. 28, 2014

(54) SYSTEM AND METHOD FOR TRAINING HUMAN SUBJECTS TO IMPROVE OFF-AXIS NEUROMUSCULAR CONTROL OF THE LOWER LIMBS

(75) Inventors: Li-Qun Zhang, Wilmette, IL (US); Hyung-Soon Park, Rockville, MD (US); Yupeng Ren, Chicago, IL (US)

(73) Assignee: Rehabtek LLC, Wilmette, IL (US)

( * ) Notice: Subject to any disclaimer, the term of this patent is extended or adjusted under 35 U.S.C. 154(b) by 1055 days.

(21) Appl. No.: 12/532,622

(22) PCT Filed: Mar. 24, 2008

(86) PCT No.: PCT/US2008/058078
§ 371 (c)(1),
(2), (4) Date: Oct. 27, 2009

(87) PCT Pub. No.: WO2008/116228
PCT Pub. Date: Sep. 25, 2008

(65) Prior Publication Data
US 2010/0145233 A1    Jun. 10, 2010

Related U.S. Application Data

(60) Provisional application No. 60/919,401, filed on Mar. 22, 2007.

(51) Int. Cl.
*A63B 24/00* (2006.01)
*A63B 5/22* (2006.01)

(52) U.S. Cl.
USPC .................................. 482/52; 482/8; 601/27

(58) Field of Classification Search
USPC ......... 482/51–53, 57, 79–80, 93, 136; 601/27
See application file for complete search history.

(56) References Cited

U.S. PATENT DOCUMENTS

| | | | |
|---|---|---|---|
| 5,967,944 A | 10/1999 | Vittone et al. | |
| 6,458,060 B1 | 10/2002 | Watterson et al. | |
| 6,830,538 B2 * | 12/2004 | Eschenbach | 482/52 |
| 6,855,094 B1 | 2/2005 | Maresh | |
| 7,090,621 B2 | 8/2006 | Loane | |
| 7,101,330 B2 | 9/2006 | Elbaz et al. | |
| 7,166,067 B2 | 1/2007 | Talish et al. | |
| 8,197,425 B2 * | 6/2012 | Kobayashi et al. | 600/595 |
| 2006/0229170 A1 * | 10/2006 | Ozawa et al. | 482/92 |
| 2007/0099762 A1 * | 5/2007 | Stevens | 482/52 |
| 2008/0116228 A1 | 5/2008 | Ryan et al. | |

OTHER PUBLICATIONS

International Search Report and Written Opinion (App. No. PCT/US2008/058078) (Sep. 25, 2008).

\* cited by examiner

*Primary Examiner* — Stephen Crow (57) ABSTRACT

Anterior cruciate ligament (ACL) is the most commonly injured knee ligament in sports-related activities, especially in pivoting sports. Considering that the knee is free to flex/extend but has much more limited motions about the off-axes (tibial rotation and valgus/varus), ACL injuries are often associated with excessive off-axis loadings. A pivoting/sliding mechanism combined with sagittal plane movement/exercise is described as a diagnostic tool to evaluate off-axis neuromechanical and anatomical risk factors of noncontact ACL injuries. The pivoting/sliding mechanism is also described as an intervention tool for off-axis training, possibly based on the diagnosis, to reduce the incidence of ACL injuries. Training outcome can also be evaluated using the pivoting/sliding mechanism. In general, the pivoting/sliding mechanism can be used with many sagittal plane exercise machines and used to improve off-axis control of the lower limbs and reduce lower limb injuries.

18 Claims, 12 Drawing Sheets

SYSTEM AND METHOD FOR TRAINING HUMAN SUBJECTS TO IMPROVE OFF-AXIS NEUROMUSCULAR CONTROL OF THE LOWER LIMBS

CROSS REFERENCES TO RELATED APPLICATIONS

This application claims priority from U.S. Provisional Application No. 60/919,401, filed on Mar. 22, 2007, and PCT/US2008/058078, filed Mar. 24, 2008, which are hereby incorporated by reference and is assigned to assignee of the present invention.

FIELD OF INVENTION

The present invention relates to the field of exercise training and injury prevention and rehabilitation.

BACKGROUND

Musculoskeletal injuries of the lower limbs are associated with the strenuous sports and recreational activities. The knee was the most often injured body area, with the anterior cruciate ligament (ACL) as the most frequently injured body part overall. Approximately 80,000 to 250,000 ACL tears occur annually in the U.S. with an estimated cost for the injuries of almost one billion dollars per year. The highest incidence is in individuals 15 to 25 years old who participate in pivoting sports. Considering that the lower limbs are free to move in the sagittal plane (e.g., knee flexion/extension, ankle dorsi-/plantar flexion), musculoskeletal injuries generally do not occur in sagittal plane movements. On the other hand, joint motion about the minor axes (e.g., knee valgus/varus (synonymous with abduction/adduction), tibial rotation, ankle inversion/eversion and internal/external rotation) is much more limited and musculoskeletal injuries are usually associated with excessive loading/movement about the minor axes (or called off-axes). The ACL is most commonly injured in pivoting and valgus activities that are inherent to sports and high demanding activities, for example. It is therefore critical to improve neuromuscular control of off-axis motions (e.g., tibial rotation/valgus at the knee) in order to reduce/prevent musculoskeletal injuries. However, existing exercise equipment (e.g., elliptical machine, treadmill, and stair climber) focuses on the sagittal plane movement. There is a lack of convenient and effective equipment and methods to train people for strenuous and high-risk activities involving off-axis loading. Training off-axis motions such as tibial rotation or valgus in isolation is unlikely to be practical and effective. A training program that addresses the specific issue of off-axis movement control during sagittal plane stepping/running functional movements will be helpful in preventing musculoskeletal injuries of the lower limbs during strenuous and training and in real sports activities.

SUMMARY OF THE INVENTION

An off-axis training and evaluation mechanism is designed to help human subjects improve neuromuscular control about the off-axes including external/internal tibial rotation, valgus/varus, inversion/eversion, and sliding in mediolateral, anteroposterior directions, and their combined motions (change the "modifiable" factors and reduce the risk of ACL and other lower limb injuries). Practically, an isolated tibial pivoting or frontal plane valgus/varus exercise against resistance in a seated posture, for example, is not closely related to functional weight-bearing activities and may not provide effective training. Therefore, off-axis training is combined with sagittal plane movements to make the training more practical and potentially more effective. In practical implantations, the off-axis training (e.g., pivoting/sliding) mechanism can be combined with various sagittal plane exercise/training machines including the elliptical machines, stair climbers, stair steppers, and exercise bicycles. Furthermore, the off-axis training (e.g., pivoting/sliding) mechanism can be implemented for an individual off-axis such as pivoting mechanism only or the sliding mechanism only, or it can be implemented in the combined axes such as pivoting-sliding mechanism.

BRIEF DESCRIPTION OF THE DRAWINGS

FIG. 9. The pivoting mechanism which can be combined with a tilting mechanism with controlled inversion/eversion and/or dorsiflexion/plantar flexion to form a pivoting-tilting mechanism. With rear end of the footplate resting on a ball-socket joint 700, the two linear actuators 720 (also anchored on ball-socket joints at both ends 730 and 740) can perturb the footplate and move it into target positions in inversion/eversion and/or in dorsiflexion/plantar flexion. The pivoting-tilting mechanism can be combined with a sagittal plane training machine such as an elliptical machine or stair climber to perform pivoting/tilting training during sagittal plane movement. The footplate pivoting and tilting are controlled by a rotary motor through a cable mechanism and a linear motor, respectively. Various perturbations in pivoting and/or in tilting can be applied flexibly. The footplate can also be controlled as "backdrivable" and free to rotate/tilt.

LIST OF REFERENCE NUMERALS

100. Servo motor for the pivoting function
110. Gear head
120. Torque sensor
130. Small cable pulley for transferring the pivoting movement
140. Supporting beams
150. Big cable pulley for driving the pivoting movement
160. Cable for the torque and rotation transmission
170. Arrow indicating Foot Sliding movement
171. Arrow indicating Foot Pivot movement
180. Left side assembly
190. Right side assembly
200. Shoe holding plate
210. Shoe side blocks
220. Toe clip
230. Shoe side clips
300. Supporting plate for holding the whole setup
310. Back linear bearing guide
311. Front linear bearing guide
320. Small supporting plate for holding the pivoting setup
330. Safety block for the pivoting exercise
400. Servo motor for the sliding function
410. Medial safety block for the sliding exercise
411. Lateral safety block for the sliding exercise
420. L-shape link for transferring the sliding force and movement
430. Linear guide driven by the servo motor
440. Force sensor
450. Small L-shape link
500. Servo motor
501. Gear head
510. Sliding block
520. Linear guide driven by the servo motor
530. Setup for inversion and eversion of the foot movement
540. Arrow indicating medial and lateral movement
541. Arrow indicating forward and backward movement
542. Arrow indicating inversion and eversion movement
600. Big cable pulley for driving the pivoting movement
610. Cable pulley
620. Cable
630. Cable pulley
640. Cable pulley
650. Cable holder
660. Arrow indicating pivoting movement driven by cables
700. Back ball-socket joint
710. Mounting plate
720. Right Linear actuator
730. Support ball-socket joint
740. Top ball-socket joint
750. Left Linear actuator
1000. Popular exercise device (Elliptical Machine)
1010. Mounting space on the popular exercise device
1020. Potentiometer cable
1030. Potentiometer for measuring the moving cycle 2010. Pivoting and sliding mechanism mounting on the left side
2020. Pivoting and sliding mechanism mounting on the right side
3000. Mounting base
3010. Rotating beam
3020. Big pulley disk for transferring the pivoting movement
3030. Cable pulley
3040. Cable pulley
3050. Cable
3060. Passive damping mechanism

DETAILED DESCRIPTION OF THE INVENTION

The invention is about off-axis training and evaluation in general including multiple off-axes and applicable to multiple sagittal plane exercise machines. In the following, application of the combined pivoting and sliding mechanism to an elliptical machine is focused on and used as an example for simplicity.

A Novel Pivoting/Sliding Elliptical Machine

Figure 1A:
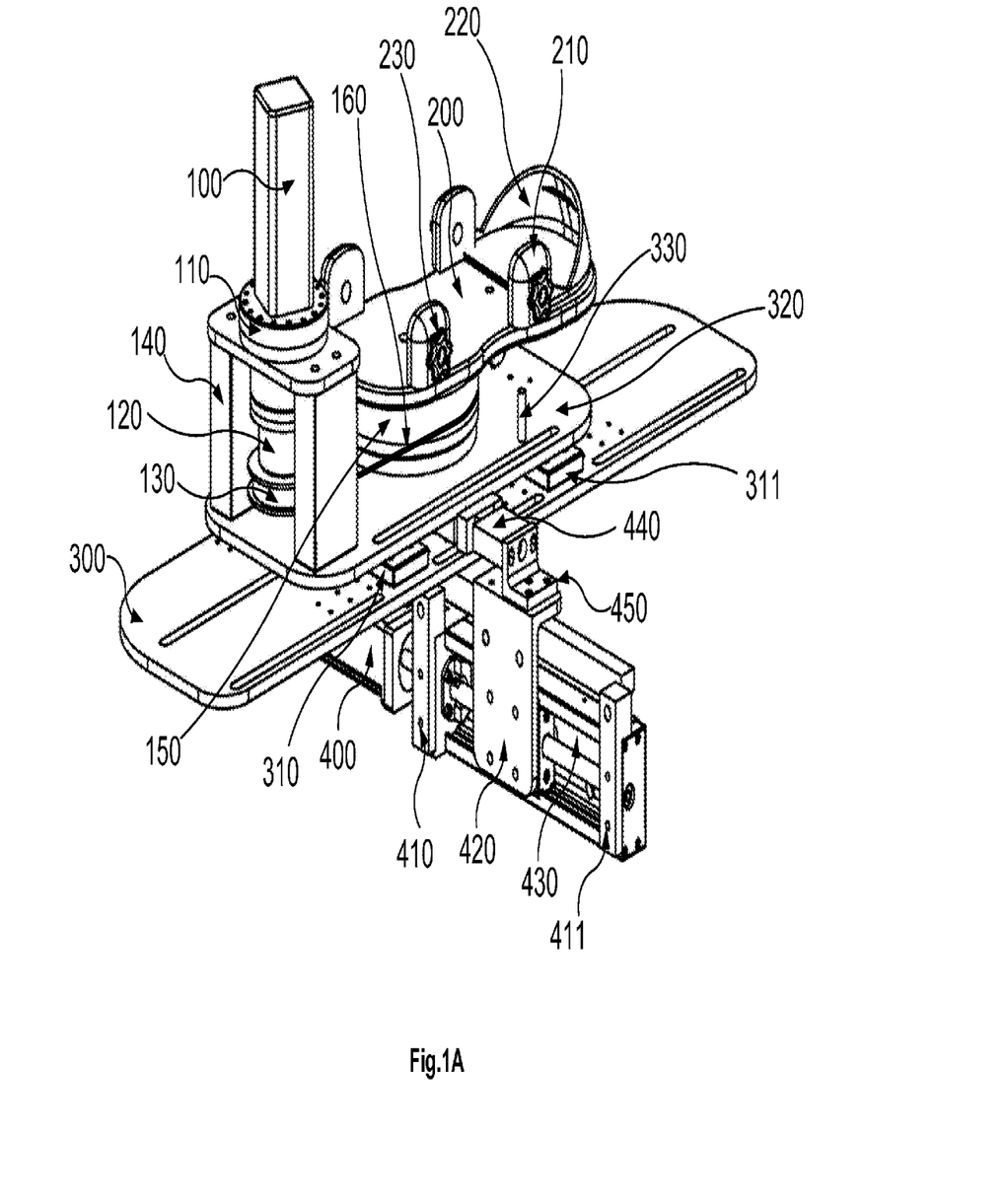
FIG. 1A. A pivoting-sliding mechanism combined with controlled tibial rotation (pivoting) and mediolateral sliding, which can be combined any sagittal plane exercise machine for off-axis as well as sagittal plane training and evaluations. The footplate rotation and mediolateral sliding are controlled by two servomotors and various combinations of perturbations can be applied flexibly.
Figure 1B:
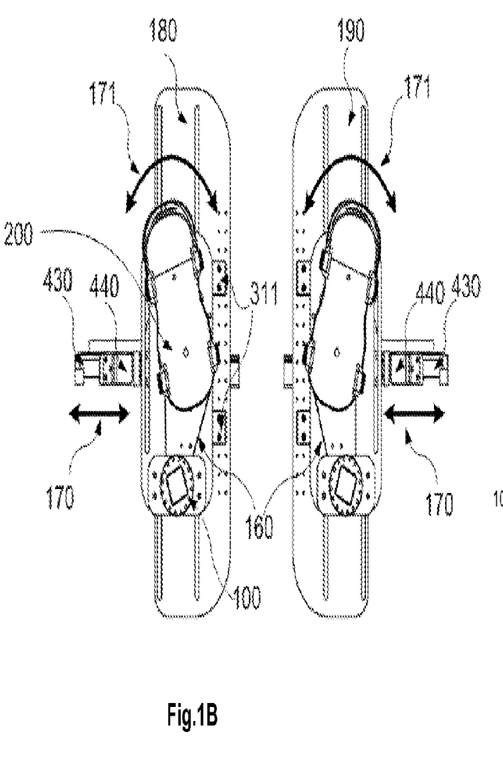
FIG. 1B. Top view of the pair of pivoting-sliding mechanisms.

The traditional footplates of an elliptical machine are replaced with a pair of custom pivoting-sliding mechanism (FIG. 1A). The subject stands on each of the pivoting-sliding mechanism through a rotating disk, which is free to rotate about the tibial rotation axis. The subject's shoes are mounted to the rotating disks through a toe strap and medial and lateral shoe blockers (or use a mechanism like a snowboard binding mounted on the rotating disk), which makes the shoe rotate together with the rotating disk while allows the subject to get off the machine easily (FIG. 1A and FIG. 1B). Each rotating disk is controlled by a servomotor through a cable-driven mechanism (FIG. 1A). An encoder and a torque sensor mounted on the servomotor measure the pivoting angle and torque, respectively (FIG. 1A).

The pivoting mechanism including the rotating disk and controlling motor (FIG. 1A) will be mounted on a pair of linear guides (with mechanical limits/stops at both ends) and controlled by a linear motor in the mediolateral direction (FIG. 1A and FIG. 1B). The mediolateral movement causes perturbation in knee valgus/varus. The foot rotation and the mediolateral movements can be controlled individually for isolated pivoting or valgus training, or they can be controlled simultaneously for combined pivoting and valgus movements. Combined with the sagittal movement, the machine can potentially be programmed to generate 3-D movement synchronized with the stepping cycle (FIG. 1C).

Figure 1C:
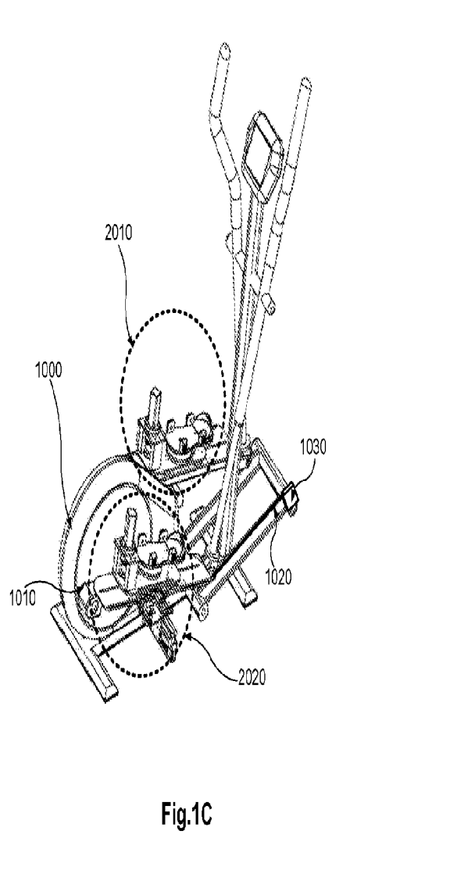
FIG. 1C. The pivoting-sliding mechanism combined with an elliptical machine with controlled tibial rotation (pivoting) and mediolateral sliding (knee valgus/varus) during sagittal plane stepping/running movement.
Figure 10:
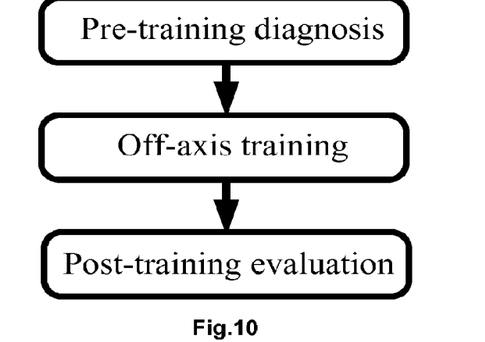
FIG. 10. A flow chart showing the integrated training with pre-training diagnosis, off-axis training, followed by post-training evaluations.

A linear position sensor is used to measure the linear movement of the sliding wheel on the ramp and thus determine the stride cycle of the elliptical movement (FIG. 1C). 0% corresponds to the highest position of the sliding wheel on the ramp and a full cycle corresponds to a stride (FIG. 1C). If needed, surface EMG can be used to evaluate the activation patterns of muscles in the lower limb to investigate which muscles are activated at what phase of the elliptical movements and to study the influence of tibial rotation/valgus movements, elliptical movement direction (forward and backward), and slope of the sliding ramp on muscle activities (FIG. 10).

Training in pivoting/sliding control can be done under the motor control in two modes:

1. The footplate is perturbed back and forth by tibial rotation (pivoting) torque and/or frontal plane mediolateral sliding force during the sagittal plane stepping/running movement. The subject is asked to resist the foot/tibial rotation torque and/or mediolateral foot-sliding force, and keep the foot pointing forward and lower limb aligned properly while doing the sagittal movements. Perturbations are applied to both footplates simultaneously during the pivoting/sliding elliptical training. The perturbations will be random in timing or have high frequency so the subject can not predict and reaction to the individual perturbation pulses. The tibial rotation/mediolateral perturbation torque/position amplitude, direction, frequency, and waveform can be adjusted conveniently. The perturbations will be applied throughout the exercise but can also be turned on only for selected time if needed.

2. The footplate is made free to rotate/slide and the subject needs to maintain stability and keep the foot straight and lower limb properly aligned during the elliptical stepping/running exercise.

Both modes are used to improve neuromuscular control in tibial rotation and/or valgus/varus.

Figure 2A:
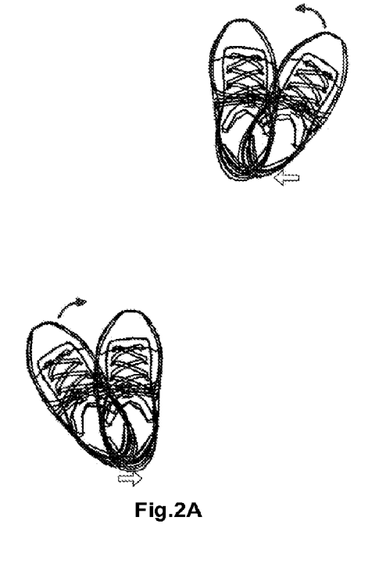
FIG. 2A. Real-time feedback used for the pivoting-sliding elliptical training. The subject is asked to follow the virtual reality (VR) cues and keep the feet pointing forward as indicated by the target shoe positions during the sagittal stepping movement.
Figure 2B:
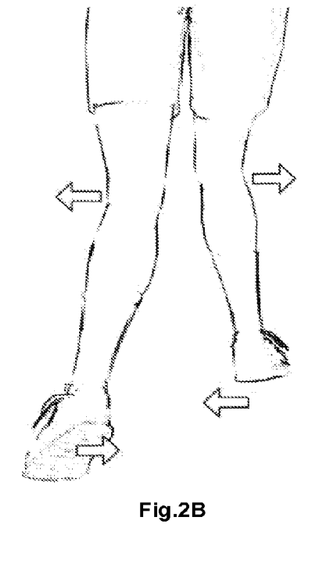
FIG. 2B. shows the real-time feedback used for the pivoting-sliding elliptical training. A web camera is used to capture and display the lower limb posture in real time, which helps the subject align the lower limbs properly in the frontal plane. Target lower limbs and shoe positions are indicated by the arrows to help the subject reach desired target limb/foot positions.

Training Off-Axis Neuromuscular Control Using the Pivoting/Sliding Elliptical Machine Real-time feedback of the footplate position is used to update a virtual reality display of the feet, which is used to help the subject achieve proper foot positioning (FIG. 2A). A web camera is used to capture the lower limb posture, which is played in real-time to provide qualitative feedback to the subject to help keep the lower limbs aligned properly (FIG. 2B).

The measured footplate rotation/slide is closely related to the pivoting/sliding movements. However, if tibial rotation/valgus angles need to be monitored more accurately, a knee goniometer can be used to measure 6-DOF knee kinematics.

Among the muscles crossing the knee, the hamstrings and gastrocnemius muscles have strong off-axis actions in controlling tibial rotation and valgus/varus. Therefore, they are expected to get strengthened through the pivoting elliptical training. Furthermore, lateral hamstring and medial gastrocnemius muscles have significant off-axis action in external tibial rotation. So if control in external tibial rotation needs to be improved based on the subject-specific diagnosis, these muscles are targeted for strengthening. If needed, real-time feedback from the EMG signals of these muscles can be used. On the other hand, the medial hamstring and lateral gastrocnemius muscles are targeted in particular if control in internal tibial rotation needs to be improved. Of note is that for more precise control, both agonist and antagonist muscles may be involved. Therefore, both medial and lateral hamstrings and both medial and lateral gastrocnemius muscles need to be trained but with the medial and lateral sides strengthened differentially (to different degrees).

The pre-training diagnosis/evaluation of off-axis neuromechanical properties in tibial rotation/valgus and the ACL-notch geometries and likelihood of ACL impingement during external tibial rotation and valgus are used to guide the subject-specific training on the pivot-sliding elliptical machine for the study group. The rotation/sliding direction that should be stronger and the specific amplitude for the internal and external rotation directions and for the valgus/varus are tailored according to the pre-training diagnosis. If the training needs to be focused on a certain direction, the servomotors are controlled accordingly and apply stronger perturbations in the desired direction. For example, if a subject has specific deficits in external tibial rotation such as high laxity/instability, low muscle strength, less sensitive proprioception, and/or slow reaction, training on the pivoting/sliding elliptical machine are focused on the external tibial rotation. The perturbations to the footplate are set stronger/quicker and more time is spent in external tibial rotation. Overall, the subjects are trained in both external and internal tibial rotations during the back-and-forth movement, which likely improve neuromuscular control in tibial rotation in general but emphasis is placed on the direction identified as the risk factors. Similar principles are used to guide training in valgus/varus with the training tailored according to the diagnosis. Furthermore, training may focus on combined off-axis loadings. For example, if a female subject is identified as having high susceptibility of ACL impingement against the lateral notch wall due to her 'narrow' notch geometry and high tibial external rotation/valgus laxity, training emphasis will be placed in the combined external tibial rotation and valgus direction. The pivoting/sliding elliptical machine will be programmed to apply more intense combined loading and with more training time in the external tibial rotation and valgus direction.

Overall, the amplitude of perturbation applied to the footplate rotation/sliding during the elliptical movement starts from moderate level and increase to a higher level of perturbations, within the subject's comfort limit. The subjects are encouraged to exercise at the level of strong tibial rotation/valgus perturbations. The perturbations can be adjusted within pre-specified ranges to insure safe and proper training. If needed, a shoulder-chest harness can be used to insure subject safety.

Figure 3A:
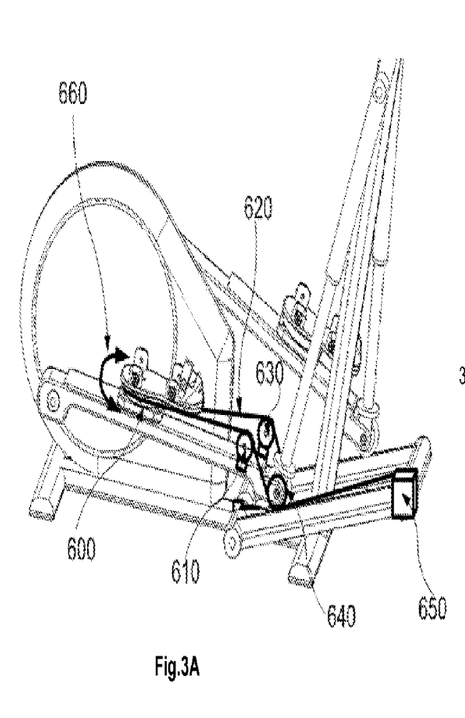
FIG. 3A. A pivoting elliptical machine with controlled pivoting (tibial rotation) during sagittal plane elliptical stepping movement, with the pivoting driven by the sagittal plane movement through cables. Movement of the sliding wheel on the ramp causes coupled rotation of pivoting disk.

Alternatively, the tibial rotation training can be done with a low-cost modified elliptical machine operating passively without a motor with such an example shown in FIG. 3A. A leather cable couples the linear movement of the sliding wheel with the rotation of the pivoting disk, and as the subject performs the elliptical movement, the footplate is rotated back and forth in tibial rotation. The rotating torque level can be adjusted by adjusting the tension of the cable-pulley system. The subject is asked to resist the rotation and keep the foot straight during the elliptical movement (FIG. 3A). As another exercise mode, the leather cable can be made loose and the pivoting disk is thus free to rotate. The subject needs to keep the legs stable in tibial rotation during the elliptical movement (FIG. 3A). Motors will not be needed in either the coupled tibial rotation mode or the free tibial rotation mode using the leather cables.

Figure 3B:
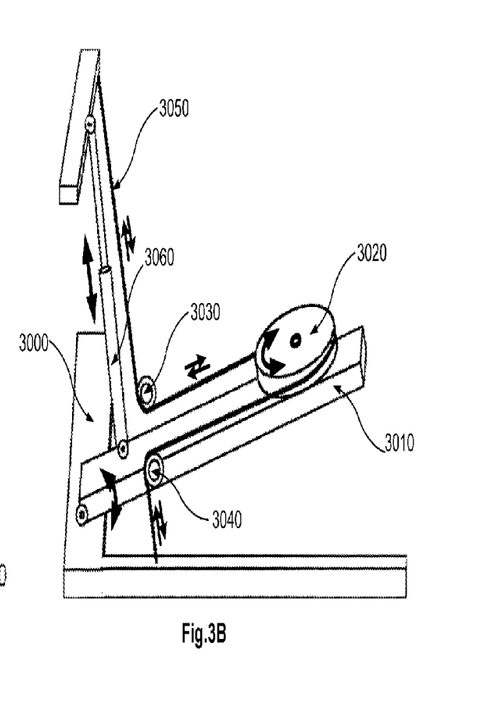
FIG. 3B. A stair climber with added movement and training in tibial rotation, for training and exercises in pivoting. Through the cable arrangement, the stepping movement of the stair climber causes coupled rotation of the footplate. A turn-buckle can be used to adjust the tension of the cable and the coupling between the sagittal stair climbing and pivoting movements.

The off-axis training can be similarly done with other exercise machines. For example, an alternative is a modified stair climber with the same principle of coupled tibial rotation during stepping movement: through a leather cable, the stepping movement of the stair climber is coupled with the rotation of the footplate/shoe (FIG. 3B) and can be used to train neuromuscular control in tibial rotation.

Figure 4:
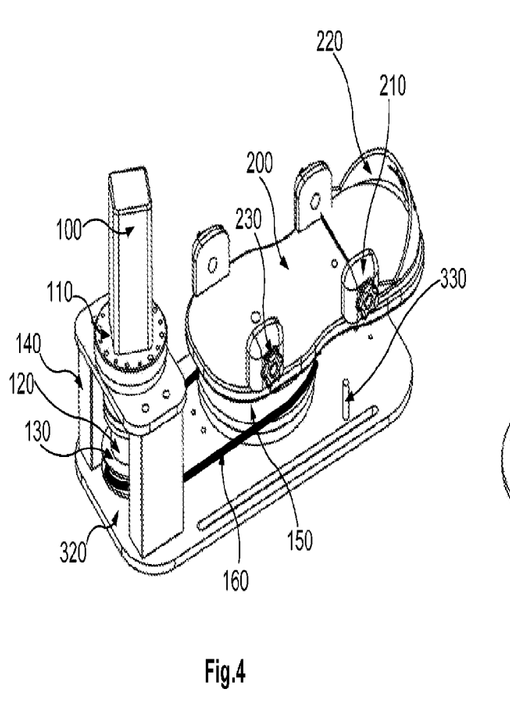
FIG. 4. A pivoting mechanism with controlled tibial rotation (pivoting), which can be combined with sagittal movement using various exercise machines. The footplate rotation is controlled by a servomotor and various perturbations can be applied flexibly. The footplate can also be controlled as "backdrivable" and free to rotate.
Figure 5:
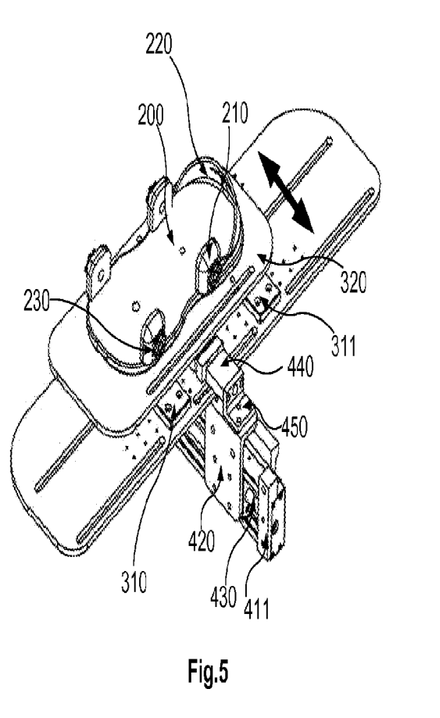
FIG. 5. A sliding mechanism with controlled mediolateral sliding, which can be combined with sagittal movement. The footplate sliding is controlled by a linear motor and various perturbations can be applied flexibly. The footplate can also be controlled as "backdrivable" and free to slide.

Combined pivoting and sliding perturbations to the foot plate may be rather challenging for the subject to deal with. Considering that external tibial rotation may be coupled with valgus in various functional movements, training in tibial rotation alone will likely help improve valgus control as well. Furthermore, it is more practical to rotate the foot and tibia, while it is difficult to abduct the knee voluntarily. Therefore, for simplified/easier training, a pivoting elliptical machine can be developed for focused training in tibial rotation (FIG. 4). Similarly, if the training/evaluation needs to be focused on the frontal plane, a mediolateral sliding only mechanism can be used (FIG. 5). Alternatively, the sliding (pivoting) mechanism in the pivoting/sliding mechanism in FIG. 1B can be locked for pivoting-only (sliding only) training.

The pivoting (or pivoting/sliding) training using the pivoting/sliding device may involve ankle and hip as well as the knee. However, considering the trunk and entire lower extremities are involved in an injury scenario in pivoting sports, it is more appropriate to train the whole lower limb together instead of training the knee in isolation. Therefore, the pivot/sliding training is useful for the purpose of lower limb injury prevention and/or rehabilitation with the multiple joints involved.

Figure 6:
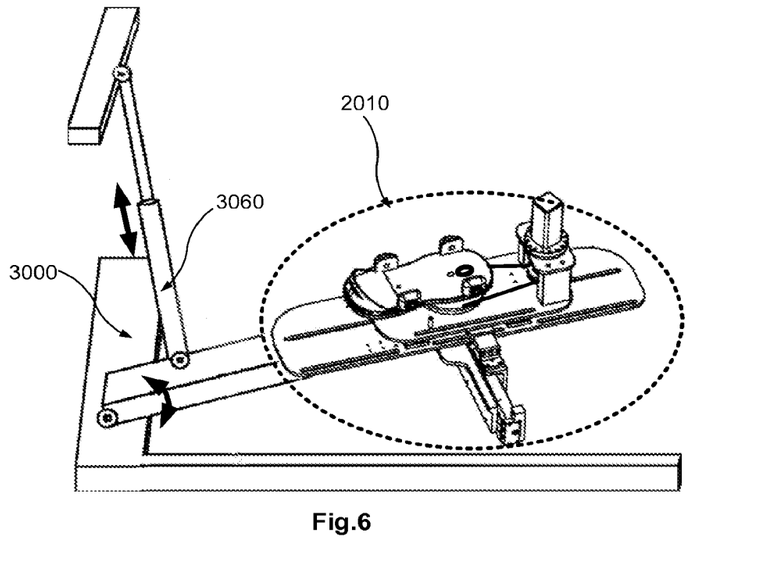
FIG. 6. The pivoting-sliding mechanism 2010 combined with a stair climber with controlled tibial rotation (pivoting) and mediolateral sliding (knee valgus/varus) during sagittal plane stair-climbing movement. The footplate pivoting and sliding are controlled by a rotary motor through cable and a linear motor, respectively. Various perturbations in pivoting and/or in sliding can be applied flexibly. The footplate can also be controlled as "backdrivable" and free to rotate/slide.

In general, the off-axis training can be combined with many sagittal plane training machines. The pivoting-sliding assembly 2010, for example, can be combined with a stair climber with controlled tibial rotation (pivoting) and mediolateral sliding (knee valgus/varus) during sagittal plane stair-climbing movement (FIG. 6).

Figure 7:
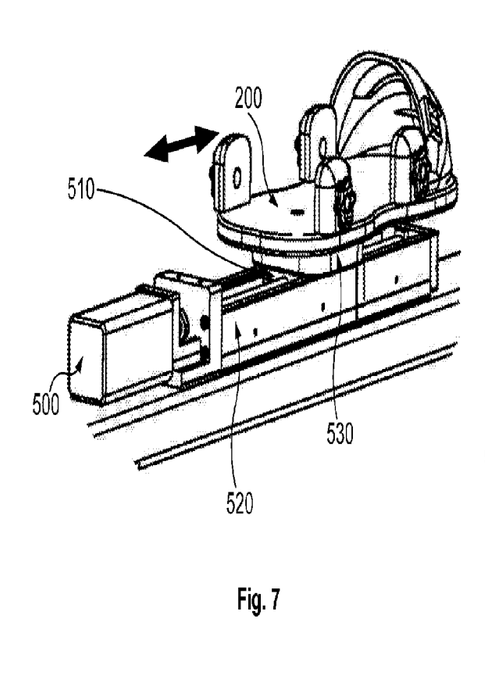
FIG. 7. A sliding mechanism with controlled anteroposterior sliding, which can be combined with sagittal movement. The footplate sliding is controlled by a linear motor and various perturbations can be applied flexibly. The footplate can also be controlled as "backdrivable" and free to slide.

Other perturbations and free movements can be similarly implemented. For example, a sliding mechanism with controlled anteroposterior sliding can be combined with a sagittal training machine (FIG. 7). The footplate sliding is controlled by a linear motor and various perturbations and "backdrivable" free to sliding can be implemented flexibly (FIG. 7). Slippery during the sagittal stepping/running, for example, can be simulated and potentially used for fall-prevention training.

Figure 8:
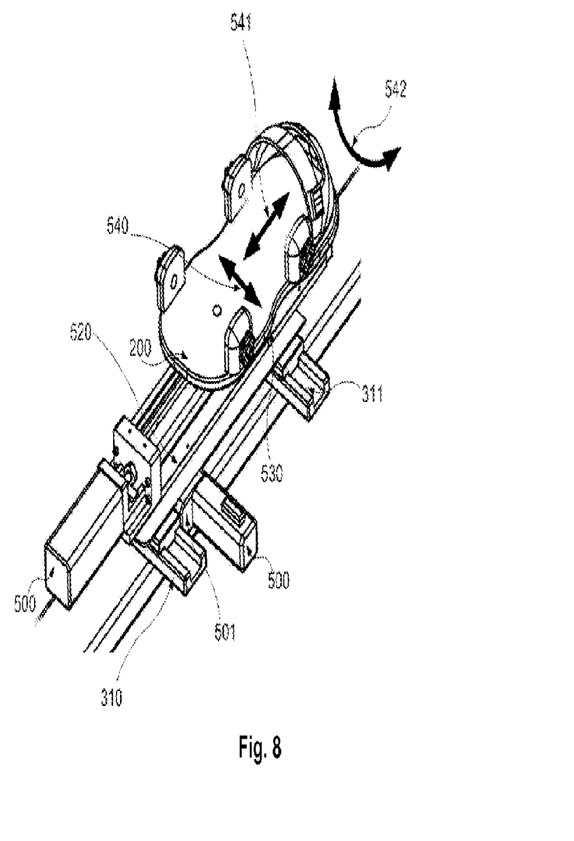
FIG. 8. A X-Y sliding mechanism with controlled anteroposterior and mediolateral slidings, which can be further combined with sagittal stepping/running movement. The footplate sliding is controlled by a pair of linear motors and various perturbations can be applied flexibly. The footplate can also be controlled as "backdrivable" and free to slide in the anteroposterior and mediolateral directions.

Furthermore, an X-Y sliding mechanism can be used for more general sliding movement control in both mediolateral and anteroposterior directions during sagittal plane stepping/running movement (FIG. 8). Two-dimensional X-Y slippery, for example, can be simulated during sagittal stepping/running movement for fall-prevention training.

Figure 9:
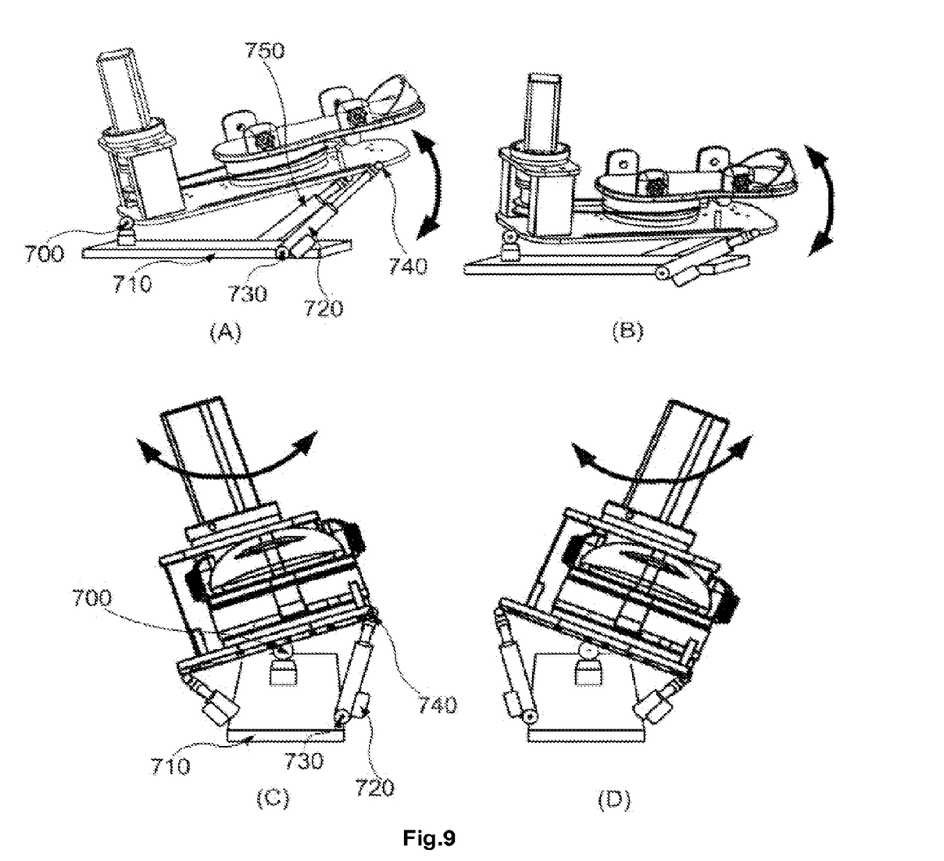

The pivoting mechanism can also be combined with a tilting mechanism with controlled inversion/eversion and/or dorsiflexion/plantar flexion to form a pivoting-tilting mechanism (FIG. 9). With the rear end of the footplate resting on a ball-socket joint 700, two linear actuators 720 (anchored on ball-socket joints at both ends 730 and 740) can perturb the footplate and move it into target positions in inversion/eversion and/or in dorsiflexion/plantar flexion. The pivoting-tilting mechanism can be combined with a sagittal plane training machine such as an elliptical machine or stair climber to perform pivoting/tilting training during sagittal plane movement. The footplate pivoting and tilting are controlled by a rotary motor through a cable mechanism and a linear motor, respectively. Various perturbations in pivoting and/or in tilting can be applied flexibly. The footplate can also be controlled as "backdrivable" and free to rotate/tilt.

Determine Training-Induced Neuromechanical Changes Using the Pivoting/Sliding Elliptical Machine Neuromechanical Diagnosis/Evaluations Using the Pivoting/Sliding Elliptical Machine The pivoting-sliding elliptical machine described for the off-axis training can also be used for pre-training diagnosis of off-axis risk factors and for post-training outcome evaluations, forming an integrated subject-specific training program (FIG. 10). The subject stands on the machine with the shoes held to the pivoting disks (FIGS. 1B and 1C). The diagnosis/evaluations can be done at various lower limb postures. The following postures can be used, for example. First, the subject stands on one leg with the knee at full extension and the contralateral knee flexed at about 45°. Measurements will be done at both legs, one side after the other. The flexed knee posture is helpful in separating the tibial rotation from femoral rotation, while the extended side provides measurements of the whole lower limb. The second posture will be the reverse of the first one. The sequence of testing is randomized to minimize the learning effect. Several measures of neuromuscular control in tibial rotation (pivoting) are taken at each of the postures as follows:

1. Stiffness: With the subject standing at a selected posture on the pivoting/sliding elliptical machine, the servomotor will apply a perturbation with controlled velocity and angle to the footplate, and the resulting pivoting rotation and torque will be measured. Pivoting stiffness will be determined from the slope of the torque-angle relationship at the common positions for both external and internal tibial rotations.
2. Energy loss: For joint viscoelasticity, energy loss will be measured as the area enclosed by the hysteresis loop.
3. Proprioception: The footplate will be rotated by the servomotor slowly (e.g., 1°/sec) and the subject will be asked to press a handheld switch as soon as she/he feels the movement. The proprioception evaluates sensing of the foot as well as tibia rotations. The perturbations will be applied randomly to the left or right leg and in the direction of either internal or external rotation. The subject will be asked to tell the side and direction of the slow movement at the time she/he presses the switch. The subject can be blind-folded to eliminate visual cues, if needed.
4. Reaction time to sudden twisting perturbation in tibial rotation: Starting with a relaxed condition, the subject's leg will be rotated at a controlled velocity and at a random time. The subject will be asked to react and resist the tibial rotation as soon as she feels the movement. Reaction time will be measured as the interval from the onset of the perturbation to the onset of the torque response generated by the subject. Several trials will be conducted, including both left and right legs and both internal and external rotation directions.
5. Stability (or instability) in tibial rotation is determined as the variation of foot rotation (in degrees) during the sagittal stepping movement.
6. Muscle strength in pivoting is measured using the pivoting elliptical machine. With the pivoting disk locked at a position of neutral foot rotation, the subject performs maximal voluntary contraction (MVC) in tibial external rotation and then in tibial internal rotation. The MVC measurements are repeated a couple of times for each direction.

The frontal plane neuromechanical properties can be evaluated using the pivoting-sliding elliptical machine, similar to the evaluations in pivoting. For example, instability in the frontal plane of the knee can be determined as the variation of foot mediolateral sliding during the sagittal stepping movement.

For pre-training diagnosis, measures from the pivoting/sliding elliptical machine can be used to identify the off-axis risk factors, which can be used to guide subsequent subject-specific off-axis training using the pivoting/sliding mechanism. Similarly, post-training outcome evaluations can be done similarly with focus on the specific risky/weak axes/DOFs for the individual subjects. Although measures obtained on the pivoting/sliding elliptical machine are not focused on the knee only, evaluations on the pivoting/sliding elliptical machine are done under close-chain condition with the whole lower limb involved, which better match the actual injury scenarios.

The pivoting/sliding elliptical machine shown in FIGS. 1A and 1C can also be used to evaluate training outcomes. The subject stands on the machine with the shoes attached to the pivoting disks (FIG. 1C). The evaluations can potentially be done at various postures. For example, the subject can stand on the left leg with the left knee at full extension and right knee flexes at about 45°. Measurements can be done at both legs, one side after the other. The flexed knee posture is helpful in separating the tibial rotation from femoral rotation, while the extended side provides measurements of the whole lower limb. The second posture is the reverse of the first one. Several measures of neuromuscular control in tibial rotation can be taken at the selected posture as follows:

1. Stiffness: At a selected posture during the elliptical stepping movement, the motor applies a perturbation with controlled velocity and angle to the footplate, and the resulting pivoting rotation and torque are measured. Pivoting stiffness is determined from the slope of the torque-angle relationship at the common positions and at controlled torque levels.
2. Energy loss: For joint viscoelasticity, energy loss is measured as the area enclosed by the hysteresis loop.
3. Proprioception: The footplate is rotated by the motor at a standardized slow velocity and the subject is asked to press a handheld switch as soon as he/she feels the movement. The perturbations are applied randomly to the left or right leg and internal or external rotation. The subject is asked to tell the side and direction of the slow movement at the time she presses the switch. The subject is asked to close the eyes to eliminate visual cues.
4. Reaction time to sudden twisting perturbation in tibial rotation: Starting with a relaxed condition, the subject's leg is rotated at a controlled velocity and at a random time. The subject is asked to react and resist the tibial rotation as soon as she feels the movement. Several trials are conducted, including both left and right legs and both internal and external rotation directions.
5. Stability (or instability) in tibial rotation is determined as the variation of foot rotation (in degrees) during the elliptical stepping movement.
6. Muscle strength in pivoting is measured using the pivoting elliptical machine. With the pivoting disk locked at a position of neutral foot rotation, the subject performs maximal voluntary contraction (MVC) in tibial external rotation and then in tibial internal rotation. The MVC measurements are repeated twice for each direction.

Figure 11A:
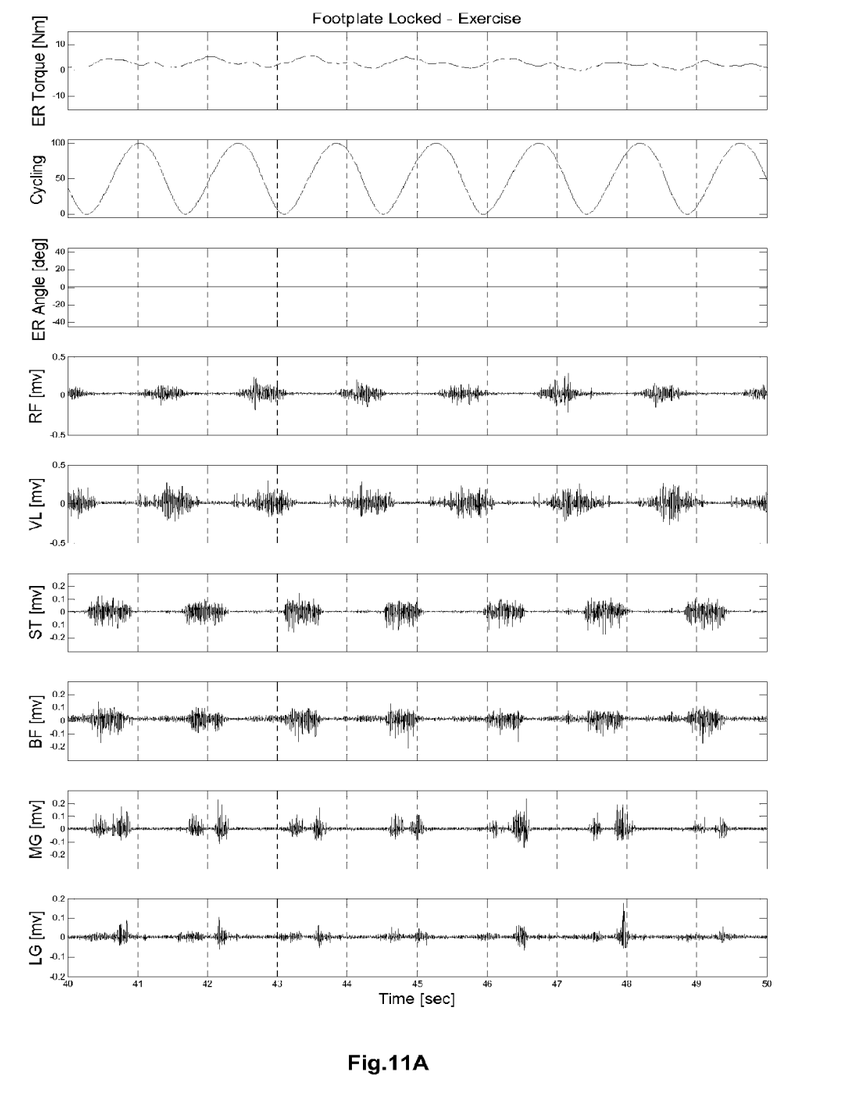
FIG. 11A. The subject performed the pivoting elliptical exercise using the novel pivoting elliptical machine. The footplates were locked in the elliptical movement.
Figure 11B:
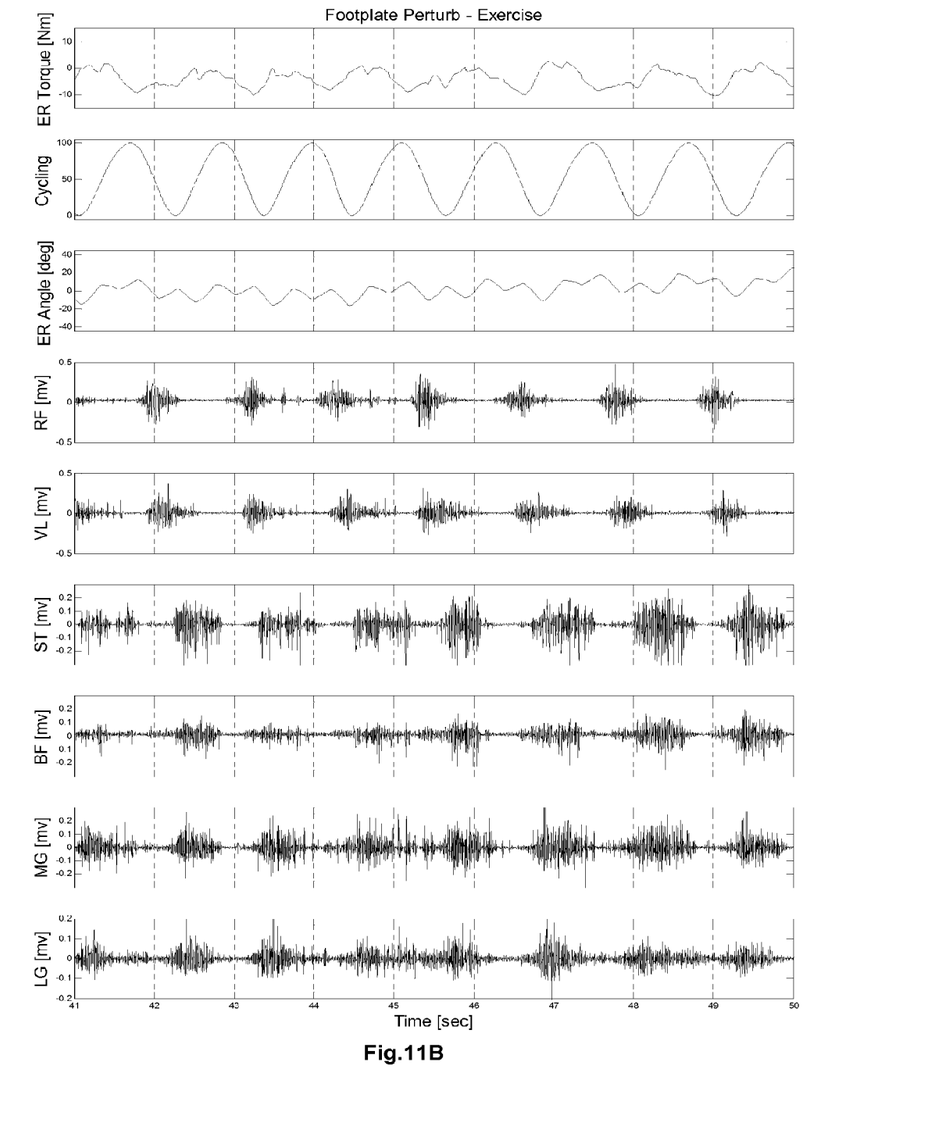
FIG. 11B. The footplates were perturbed by a series of torque pulses which rotate the footplates back and forth. The subject was asked to perform the elliptical movement while maintaining the foot pointing forward. Notice that the enhanced muscle activities when the subject performed the elliptical movement with rotation perturbations. From top to bottom, the plots show the footplate external rotation torque (tibial internal rotator muscle generated torque was positive), sliding wheel position (a measurement of elliptical cycle), footplate rotation angle (external rotation is positive), and EMG signals from the rectus femoris, vastus lateralis, semitendinosus, biceps femoris, medial gastrocnemius, and lateral gastrocnemius.

Improvements Through Off-Axis Pivoting Training Using the Pivoting Elliptical Machine Human subject can easily get used to the elliptical movement with rotational pivoting perturbations at both feet and perform the pivoting elliptical movement naturally. The rotational perturbations result in stronger muscle activities in the targeted lower limb muscles. The hamstrings and gastrocnemius activities are increased considerably during forward elliptical movement with the perturbation, for example, as shown in FIGS. 11A and 11B.

Figure 12A:
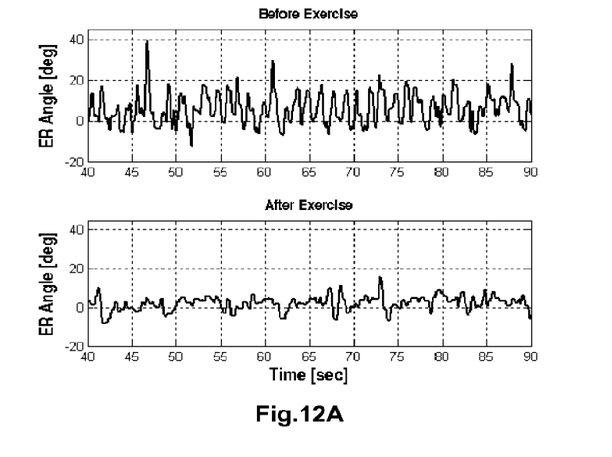
FIG. 12A. Stability in tibial rotation during the pivoting elliptical exercise before and after 5 sessions of training using the pivoting elliptical machine. The data are from the same female subject. Notice the considerable reduction in rotation angle variation and thus improvement in rotation stability.
Figure 12B:
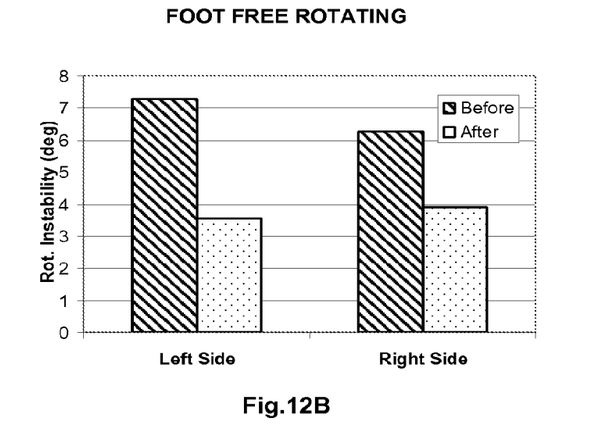
FIG. 12B Rotation instability of a female subject before and after 5 sessions of training during forward elliptical exercise with foot free to rotate. Similar results were observed in backward pivoting elliptical movements.
Figure 12C:
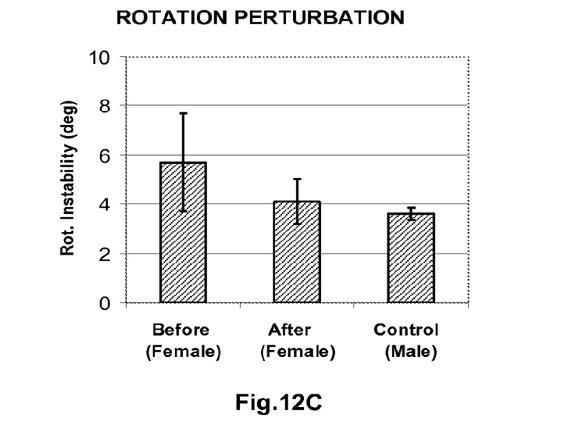
FIG. 12C Rotation instability of multiple subjects before and after 5 sessions of training during forward pivoting elliptical exercise with footplate perturbed in rotation by the motor.

Improvement in sensory-motor performance through the pivoting elliptical training is observed. Over five 30-minute training sessions, the subjects showed marked improvement in controlling tibial rotation, as shown in the reduced rotation instability (variation in rotation) (FIG. 12A). The pivoting disks were made free to rotate and the subject was asked to keep the feet stable and pointing forward during the elliptical movements. Standard deviation of the rotating angle during the pivoting elliptical exercise was used to measure the rotating instability, which was reduced markedly after the training (FIG. 12A), and the instability reduction was obvious for both left and right legs (FIG. 12B). Similar results were seen for both forward and backward elliptical movements. Interestingly, the instability of the dominant right side was generally lower than the non-dominant left side, considering that the subjects involved were all right-handed. Similar improvement was observed for rotation instability measured under external perturbation of the footplate by the motor, as shown in FIG. 12C, which also showed higher rotation instability of females as compared with males. The increased stability following the training may be related to improvement in tibial rotation muscle strength, which was increased after the training of multiple sessions.

Figure 13A:
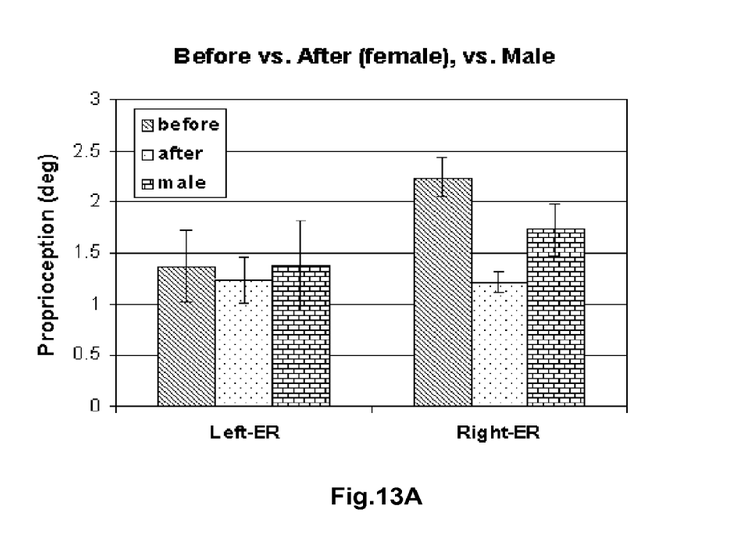
FIG. 13A. Proprioception of the female subjects before and after 5 sessions of training, and the males (before training only).
Figure 13B:
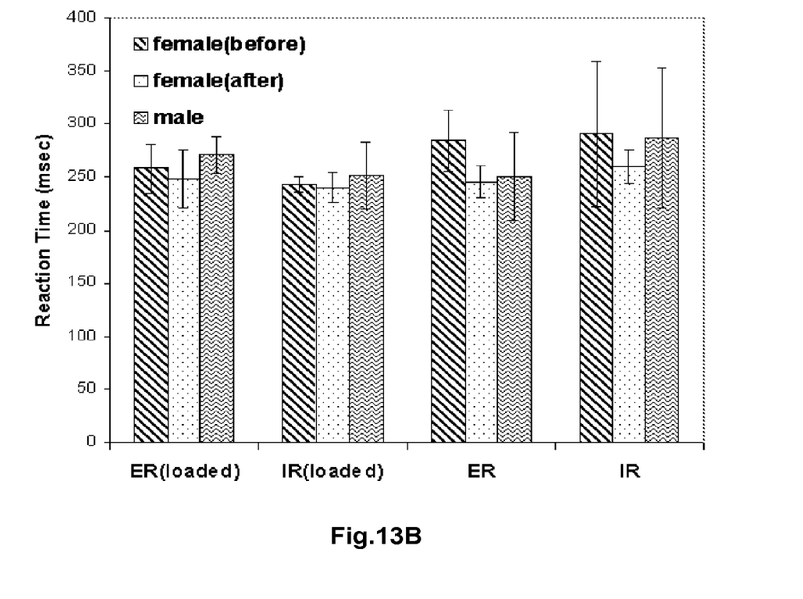
FIG. 13B (b) Reaction time of the female subjects before and after 5 sessions of training, and between females and males (before training only). The subject stood on the left leg (100% body load) on the pivoting elliptical machine with the right knee flexed and unloaded (0% body load). From left to right, the 4 groups of bars correspond to the reaction time for external rotating (ER) the loaded left leg, the reaction time for internal rotating (IR) the loaded left leg; the reaction time for external rotating the unloaded right leg; and the reaction time for internal rotating the unloaded right leg.

Proprioception in tibial rotation also showed improvement with the training, as shown in FIG. 13A. In addition, reaction time tends to be shorter for the loaded leg as compared to the unloaded one and tendency of training-induced improvement was observed (FIG. 13B).

What is claimed:

1. A lower-limb training apparatus that implements off-axis functional motions of a user, said lower limb training apparatus comprising:
 a sagittal plane exercise machine for major lower limb movement within a human sagittal plane in use, and a mount for an off-axis movement mechanism;
 an off-axis movement mechanism coupled to said mount for performing a secondary off-axis motion of the lower limbs,
 and a footplate arranged to hold a user's foot and coupled with the off-axis movement mechanism
 wherein said off-axis movement mechanism comprises at least one of:
  (1) a pivoting mechanism that includes a disk arranged to rotate about a tibial rotation axis of a user, wherein said secondary off-axis motion comprises a pivoting perturbation of said footplate and guides internal/external tibial rotation of the user's foot while said footplate moves in the direction of said major lower limb movement in the sagittal plane;
  (2) a sliding mechanism that includes a mediolateral slider wherein said secondary off-axis motion comprises a sliding movement of said footplate and guides a frontal plane sliding motion of the user's foot while said footplate moves in the direction of said major lower limb movement in the sagittal plane.

2. A lower-limb training apparatus according to claim 1 further comprising a position sensor for measuring the angular or slide position of said footplate and/or a force sensor for measuring a force applied to said footplate.

3. A lower-limb training apparatus according to claim 1, wherein said pivoting mechanism comprises a rotary motor and/or said sliding mechanism comprises a linear motor.

4. A lower-limb training apparatus according to claim 3 further comprising a controller, said controller being arranged to control said rotary and/or linear motor to apply a force to said footplate.

5. A lower-limb training apparatus according to claim 3 wherein said rotary motor and/or linear motor are arranged to apply perturbations to said footplate during said lower limb movement in the sagittal plane.

6. A lower-limb training apparatus according to claim 1 wherein said mount comprises a first mount on a left side of said sagittal plane exercise machine and a second mount on a right side of said sagittal plane exercise machine, wherein said off-axis movement mechanism comprises respective first and second off-axis movement mechanisms, each of said first and second off-axis movement mechanisms comprising a pivoting and sliding mechanism.

7. A lower-limb training apparatus according to claim 1 comprising the pivoting mechanism, wherein said apparatus further comprises a tilting mechanism for said footplate so as to accommodate controlled inversion/eversion and/or dorsiflexion/plantar flexion of the user's foot.

8. A lower-limb training apparatus according to claim 1 comprising the sliding mechanism, wherein said sliding mechanism further accommodates anteroposterior sliding of said footplate.

9. A lower-limb training apparatus according to claim 1 wherein said footplate is mounted on said pivoting disk and comprises a toe clip arranged to be tightened to accommodate shoes of differing size and/or side clips arranged to prevent a shoe from sliding laterally.

10. A lower-limb training apparatus according to claim 1 further comprising a virtual reality display indicating target user lower limb and foot positions to help the user reach desired target limb/foot positioning.

11. A lower-limb training apparatus according to claim 10, further comprising a web camera to capture the user's lower limb posture in real time for display on said virtual reality display, wherein arrows are provided on the display to indicate the desired target limb/foot positioning.

12. A lower-limb training apparatus according to claim 1, wherein said off-axis movement mechanism comprises a cable mechanism having a pulley attached to said pivoting disk and a cable wrapped around said pulley for driving said pivoting movement of said footplate.

13. A lower-limb training apparatus according to claim 1, comprising measurement means for determining joint stiffness of a user's lower limb by calculating the slope of the torque-angle relationship measurement by said position sensor and force sensor.

14. A lower-limb training apparatus according to claim 1, comprising measurement means for determining energy loss by calculating an area under a plot of position measurements against force measurements.

15. A lower-limb training apparatus according to claim 1, comprising measurement means for determining user proprioception, said measurement means comprising a handheld switch and a motor arranged to rotate said footplate at a standardized velocity so as to apply perturbations to said footplate, said perturbations being applied in random directions, wherein the proprioception is measured as the angle of pivoting movement or distance of sliding movement of said footplate from a time cue until when the user depresses the switch.

16. A lower-limb training apparatus according to claim 1, comprising measurement means for determining user reaction time, said measurement means comprising a motor arranged to rotate said footplate at a controlled velocity and at a random time, wherein the force sensor determines a user reaction to said rotation of said footplate and the reaction time is measured as the time spent until said user reaction is sensed.

17. A lower-limb training apparatus according to claim 1, wherein said sagittal plane exercise machine accommodates an elliptical stepping movement of the user's lower limb, the apparatus further comprising measurement means for determining user lower limb stability, said stability being determined as a variation in recorded tibial foot rotation or mediolateral translation during said sagittal plane exercise.

18. A lower-limb training apparatus according to claim 1, comprising measurement means for determining user muscle strength, wherein the off-axis movement mechanism comprises a lock means for locking the mechanism at a position of neutral foot rotation, the user muscle strength being determined by the force sensor in response to a maximal voluntary contraction by the user.

* * * * *